(12) United States Patent
Dartey et al.

(10) Patent No.: US 7,232,574 B1
(45) Date of Patent: Jun. 19, 2007

(54) LONG CHAIN ALCOHOLS PROVIDED IN EDIBLE OILS

(75) Inventors: Clemence K. Dartey, North Wales, PA (US); Thomas E. Sox, Ambler, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 1186 days.

(21) Appl. No.: 09/461,887

(22) Filed: Dec. 15, 1999

(51) Int. Cl.
*A61K 47/00* (2006.01)
*A61K 31/045* (2006.01)

(52) U.S. Cl. ........................ 424/439; 514/724
(58) Field of Classification Search ........... 424/439; 514/724
See application file for complete search history.

(56) References Cited

U.S. PATENT DOCUMENTS

| | | | |
|---|---|---|---|
| 3,881,005 A | 4/1975 | Thakkar et al. | 424/238 |
| 4,391,732 A | 7/1983 | Lundmark | 252/356 |
| 5,271,881 A | 12/1993 | Redding, Jr. | 264/432 |
| 5,460,756 A | 10/1995 | Redding, Jr. | 264/4 |
| 5,502,045 A | 3/1996 | Miettinen et al. | 514/182 |
| 5,663,156 A | 9/1997 | Granja et al. | 514/164 |
| 5,770,749 A | 6/1998 | Kutney et al. | 552/545 |
| 5,856,316 A | 1/1999 | Granja et al. | 514/164 |
| 5,869,708 A | 2/1999 | Das et al. | 552/510 |
| 5,892,068 A | 4/1999 | Higgins, III | 552/554 |
| 5,952,393 A | 9/1999 | Sorkin, Jr. | 514/729 |

FOREIGN PATENT DOCUMENTS

| | | |
|---|---|---|
| EP | 0 801 904 A1 | 10/1997 |
| EP | 0 901 804 | 3/1999 |
| JP | 51 11113 | 4/1976 |
| WO | WO 98/19556 | 5/1998 |
| WO | WO 98/47385 | 10/1998 |
| WO | WO 99/40922 | 8/1999 |

OTHER PUBLICATIONS

CAPLUS Abstract, AN 1994:321866, Kimura, 1994.*
CAPLUS Abstract, AN 1989:153130, Tanaka, 1989.*
CAPLUS Abstract, AN 1986:18914, Hohnen Oil Co., 1986.*
Handbook of Chemistry and Physics, 57$^{th}$ edition, 1977, Chemical Rubber Co., pp. D-216, 217, and F-56.*
*Gas Chromatographic Study of Natural Waxes*, Dr. K.H. Miltenberger, Wachs, 2(12) (1970), pp. 736-742.
Sho, H., Chinen, I., and Fukuda, N., J. Nutr. Sci. Vitaminol 30:553 (1984).
DERWENT Abstract, AN 1996-095736[10], An et al. (XP-002163880).
DERWENT Abstract, AN 1986-117166, Nippon Oils and Fats Co. Ltd. (XP 002042067).
Patent Abstracts of Japan, 1986-61064815, Kawai Jun.
Patent Abstracts of Japan, 1992-04253870, Tanaka Yoshiharu.
Patent Abstracts of Japan—JP 60049752 Mar. 19, 1985 Sanyuu Shoji KK (1983-156288).
European Search Report (Application No. EP 00 31 1174).

* cited by examiner

*Primary Examiner*—Shengjun Wang

(57) ABSTRACT

The present invention provides a method for incorporating long chain alcohols into edible oils. The long chain alcohol/edible oil admixture is then suitable for use in preparation of various foods. The long chain alcohol is added by the introduction of energy and in a preferred embodiment in the absence of surfactants and emulsifiers.

19 Claims, No Drawings

LONG CHAIN ALCOHOLS PROVIDED IN EDIBLE OILS

RELATED APPLICATIONS

This application is being concurrently filed with two additional applications. These related applications are entitled Encapsulated Long Chain Alcohols, U.S. Ser. No. 09/461,592 and Long Chain Alcohols Admixed in Sterol Compounds, U.S. Ser. No. 09/461,607, the contents of these applications incorporated by reference as if set forth in their entirety.

FIELD OF THE INVENTION

The present invention describes a method of obtaining uniform distribution of a long chain alcohol or a mixture of such alcohols in a comestible product by dissolving or suspending the long chain alcohol in an edible oil.

BACKGROUND OF THE INVENTION

Long chain alcohols are known to have beneficial effects on human health. Researchers have reported that a blend of long chain alcohols obtained from sugar cane wax was effective in lowering serum cholesterol in rats. Sho, H., Chinen, I., and Fukuda, N., J. Nutr. Sci. Vitaminol. 30:553 (1984). In addition, U.S. Pat. No. 5,856,316 discloses the use of a mixture of long chain alcohols from sugar cane wax for lowering serum cholesterol in humans.

From the above disclosures it is apparent that long chain alcohols have important properties for improving the health of humans and animals. These beneficial properties include improving stamina, lowering blood cholesterol levels, and decreasing platelet aggregation. One desirable route for ingesting these alcohols is in food or beverage products. However, these long chain alcohols are very insoluble in water, and the very small amounts of these long chain alcohols needed to produce beneficial health effects makes content uniformity of long chain alcohols in a dry blending operation very difficult to achieve. Therefore, a means is needed for incorporating these long chain alcohols into food or beverage products in a manner that yields a uniform and consistent distribution of these materials in the comestible product.

Expensive and difficult measures have been disclosed to overcome these problems. For example, EP 801904 A1, describes the use of long chain alcohols (defined as alcohols having more than 20 carbon atoms) in continuous fat phase compositions containing particulate sweeteners. The incorporation of the long chain alcohols at about 0.1% to about 0.4% was reported to decrease the viscosity of confectionery coatings made with this composition. All of the described compositions contained a particulated sweetener in addition to a chocolate material and a vegetable oil.

Similarly, WO 98/47385 discloses a fat emulsion with a blend of emulsifiers created by the blending of a partial glyceride with a phospholipid and a long chain alcohol having a chain length of greater than $C_{20}$. The total weight of the glyceride and phospholipid in the composition must be greater than about 0.02 weight percent.

Despite the teachings of these disclosures, there is an ongoing need to easily incorporate long chain alcohols into food products so that the advantageous effects of these alcohols can be achieved.

SUMMARY OF THE INVENTION

The present invention provides a method of providing a desirable distribution of long chain alcohols in a food or beverage product. More specifically, this process comprises dissolving or suspending the long chain alcohol in an edible oil, and then incorporating this edible oil into a food or beverage product. In one embodiment the present invention is a method for preparing a long chain alcohol in an edible oil material comprising: providing an edible oil substantially free of medium chain triglycerides composed of $C_8$-$C_{10}$ triglycerides and less than about 12 weight percent linolenic acid; providing a long chain alcohol; admixing said edible oil and long chain alcohol in the presence of an energy source such that the long chain alcohol is admixed in the oil; said long chain alcohol/edible oil admixture is stable and substantially free of an emulsifier or surfactant and having a viscosity of less than about 200 centipoise as measured at 70° F. at 60 revolutions per minute. A second embodiment of the invention provides the composition made by the method of the invention. In a third embodiment the composition of the present invention is employed to reduce the cholesterol level of a vertebrate that consumes an effective amount of the composition.

DETAILED DESCRIPTION OF THE INVENTION

The present invention provides a method for incorporating long chain alcohols into an oil matrix without the need to add emulsifiers, surfactants or penetrant enhancers. The method includes the use of heat or mechanical energy or other suitable energy sources in order to make the long chain alcohols soluble in the lipid matrix. In a preferred embodiment the lipid matrix is an oil, preferably an oil derived from a vegetable source. Suitable oil sources include sunflower, safflower, corn, soybean, canola, mixtures of these oils and the like.

As used herein, long chain alcohols are understood to include saturated and unsaturated alcohols which contain more than about 90 weight percent $C_{20}$ or longer, primarily aliphatic alcohol materials. For the greatest health benefit it is preferred that the long chain alcohols be predominately, greater than 50 weight, percent octacosanol ($C_{28}$), preferably more than 65 percent and more preferably greater than about 70 weight percent. As used herein policosanol is understood to be a mixture of long chain alcohols ranging from $C_{20}$ to $C_{36}$ preferably with greater than 65 weight percent $C_{28}$. Common distribution and concentration ranges of the various components of policosanol are found in U.S. Pat. No. 5,856,316, the contents of which are incorporated by reference as set forth in its entirety. These long chain alcohols are available from various natural sources, most preferably from sugar cane wax. The long chain alcohols can also be synthesized using techniques well known in the art.

Policosanol is soluble at about 160-180° F. in suitable lipid matrices such as vegetable oils and fat-soluble emulsifiers, vitamins and the like. Suitable methods for incorporating policosanol or other long chain alcohol into the oil, include heating by conventional means such as: heating elements or open flame; radiation sources and other ultrasonic wave generating equipment; as well as mechanical means such as agitation, homogenization, and the like.

In a preferred embodiment of the present invention, the long chain alcohol is ground into a microcrystalline form in order to improve the stability of the oil/long chain alcohol mixture. Suitable grinding techniques include hammermill, cryogenic rotary mills and the like. The particle size of the ground material is less than about 100 microns, preferably from about 20 to about 80 and most preferably from about 30 to about 60 microns.

Typically the level of long chain alcohol incorporated into the oil is from about 0.1 to about 5 percent, preferably from about 0.5 to about 3 and most preferably from about 0.8 to about 2 weight percent. Those with skill in the art will appreciate that the concentration of the long chain alcohol will vary depending on various factors such as the dosage desired, the serving size and the solubility of the long chain alcohol in a particular oil.

One advantage of the present invention is that the long chain alcohol remains stable in the edible oil. As used herein, stable is understood to mean that the long chain alcohol does not precipitate, crystallize out, or separate when dissolved in the edible oil.

Another advantage of the present invention is that the viscosity of the policosanol-enriched oil is such that the admixture remains suitable for many applications. Unlike other disclosures, the present invention does not have to be made into a high viscosity paste before being incorporated in a comestible. The long chain alcohol/edible oil mixture has a viscosity of less than about 200 centipoise, preferably from about 10 to about 150 and most preferably from 50 to about 130 centipoise. The viscosity is measured at 70° F. using a Brookfield Viscometer Model DV-II+, spindle #2 at 60 revolutions per minute for 10 seconds.

Once the long chain alcohol has been suspended or dissolved into the oil matrix, those with skill in the art will readily understand how to incorporate the long chain alcohol/oil matrix into food products designed to lower cholesterol. The long chain alcohol/oil preparations can be used as a spray oil for cookies and crackers or can be used to formulate a number of cholesterol lowering food products including salad dressings, mayonnaise dressings, nutrition bars, beverages, juices, low fat ice creams, yogurts and frozen yogurts, non-dairy creamers, cheese spreads, milk products, confectioneries, chocolate-containing products such as cakes and cookies, margarine, and other spreads suitable for application on breads and the like. The long chain alcohol/oil preparations can also be formulated into pharmaceutical preparations, including tablets, soft gelatin capsules, especially those containing liquid formulations, such as suspensions, emulsions, solutions and the like.

The present invention can be provided in foods in which water is the continuous phase, such as salad dressings and mayonnaise. In a preferred embodiment of the invention the long chain alcohol/edible oil product of the present invention is incorporated into a product which has a continuous oil phase such as spreads and margarines. The long chain alcohol typically comprises from about 0.0001% to about 0.4% of the comestible product, preferably from about 0.007 to about 0.14 and most preferably from about 0.018 to about 0.071 weight percent of the comestible product.

Typically the level of the long chain alcohol is from 0.1 to about 100 milligrams/servings; preferably from about 0.5 to about 20 milligrams/serving and most preferably from about 2 to about 10 milligrams/servings.

The present invention provides an edible oil/long chain alcohol mixture that does not require the incorporation of high levels of linolenic acid in the edible oil as was previously disclosed in the art. Further the present invention does not require the addition of triglycerides, particularly $C_8$-$C_{10}$ triglycerides; or other surfactants or emulsifiers in order to form the admixture. Because the edible oil/long chain alcohol does not need to incorporate these other agents, the admixture can be more readily formulated into other comestible products. Substantially free as used herein is understood to mean less than 1.0 weight percent, preferably less than 0.5 and most preferably less than 0.1 weight percent.

The comestible product of the present invention can be used to reduce the cholesterol level of vertebrates that consume the comestible. Vertebrates include reptiles, mammals, fish and the like, with humans being most preferred.

The following examples are provided as specific embodiments of the present invention. Other modifications of this invention will be readily apparent to those skilled in these arts without departing from the scope of the present invention.

EXAMPLE 1

One percent policosanol in a vegetable oil was prepared by adding 2.0 g policosanol (CHOLESSTANOL (95% pure sugarcane wax material from Garuda International)) to 198.0 g soybean salad oil in a 400-ml PYREX glass beaker. The beaker was placed in a waterbath on a stove. The stove was turned on and the soybean oil/policosanol mixture was stirred gently by hand with a stainless steel spatula. The policosanol/soybean oil dispersion was heated and stirred until policosanol melted and solubilized in the oil at 160-180° F. The viscosity of the policosanol soybean oil preparation was measured at 170, 120, 80 and 70° F. using the Brookfield Viscometer Model DV-II+, Spindle #2 @ 60 rpm for 10 seconds. This viscosity data is presented in Table 1. Table 1 also presents results on soybean salad oil preparations containing 0, 0.1, 0.2, 0.4 and 0.6 weight % policosanol made by similar processes.

The results showed no significant differences between the viscosities of the samples at 120° F. and also at 176° F. regardless of the policosanol concentration. However, at 80 and 70° F., the viscosities of the samples increased as the concentration of policosanol in the oil samples increased. The samples were stored at room temperature and observed the next day. The policosanol preparations developed translucent gel-like precipitates. After a few days at room temperature, the gel-like materials developed layers and gel-like precipitates. The gel-like precipitates dissolved when the samples were heated to about 180° F.

TABLE 1

Effect of Policosanol Concentration on Viscosity of Soybean Oil

| % Policosanol Concentration | Viscosity @ 176° F. | Viscosity @ 120° F. | Viscosity @ 80° F. | Viscosity @ 70° F. |
| --- | --- | --- | --- | --- |
| 0 | 15.0 cP | 26.0 cP | 43.3 cP | 59.5 cP |
| 0.10 | 14.5 cP | 27.0 cP | 43.5 cP | 64.5 cP |
| 0.20 | 14.5 cP | 28.0 cP | 46.5 cP | 82.0 cP |
| 0.40 | 15.0 cP | 28.0 cP | 49.5 cP | 119.0 cP |
| 0.60 | 15.0 cP | 28.0 cP | 53.5 cP | 112.0 cP |
| 1.00 | 14.5 cP | 28.0 cP | 105.0 cP | 129.0 cP |

EXAMPLE 2

A policosanol preparation from the preceding example containing 1.0% policosanol in soybean oil was used to produce cholesterol lowering regular and light (reduced fat) margarine spreads containing plant stanol esters. The formulations are shown in Table 2. The oil phase ingredients, liquid soy bean oil (#9196 Ventura) and partially hydrogenated soybean oil (#9494 Ventura), Canola oil, plant stanol esters, monoglycerides, lecithin and hexaglycerols were blended together in a margarine emulsion tank. The blend was mixed slowly and heated to 160° F. to melt into a clear liquid oil blend. The policosanol preparation, butter flavor, vitamins A & D blend and beta-carotene were added and blended into the oil phase.

The aqueous phase was prepared by blending potassium sorbate, ethylenediaminetetra acetic acid (EDTA), citric acid and salt in the water in an aqueous phase tank or in a stainless steel container. While stirring the oil phase at high speed, about 800 rpm, the aqueous phase was poured slowly into the oil phase to produce the margarine spread emulsion at approximately 130±5° F. The margarine was prepared by processing the emulsion through a scrape surface heat exchanger (A-unit) and then through a pin worker (B-unit) and finally through a filler unit. The finished margarine spread was filled into suitable containers. The cooling system was adjusted during the processing of the margarine spread emulsion to maintain the temperature of the finished spread at the filler unit at about 40-60° F. The margarine spreads processed as indicated exhibited physical and sensory properties characteristic of regular and light margarine spreads.

TABLE 2

Composition of a Typical Cholesterol-Lowering Margarine Spread Containing Policosanol.

|  | Regular Margarine Spread Wt. Pounds | Light Margarine Spread Wt. Pounds |
|---|---|---|
| Oil Phase Ingredients |  |  |
| Liquid Soybean Oil | 7.44225 | 23.64125 |
| Partially Hydrogenated Soybean Oil | 11.00000 | 0 |
| Liquid Canola Oil | 30.00000 | 0 |
| Plant Stanol Esters (Raisio) | 21.55000 | 21.55000 |
| Mono-glycerides | 0.30000 | 0.40000 |
| Lecithin | 0.20000 | 0.30000 |
| Hexaglycerol Distearate, POLYALDO 6-2-S (Lonza) | 0.10000 | 0.10000 |
| Hexaglycerol Mixed Esters, CAPROL ET (A. C. Humko) | 0 | 0.10000 |
| Butter Flavor (Firmenich) | 0.05000 | 0.05000 |
| Vitamin A & D Blend (Roche) | 0.00625 | 0.00625 |
| Beta-Carotene | 0.00150 | 0.00250 |
| Policosanol/Oil Blend, (1:99 w/w) (CHOLESSTANOL Policosanol from Garuda International) | 4.35000 | 4.35000 |
| Aqueous Phase Ingredients |  |  |
| Water | 22.88550 | 47.38300 |
| Salt | 2.00000 | 2.00000 |
| Citric Acid | 0.00750 | 0.01000 |
| Calcium Disodium EDTA | 0.00700 | 0.00700 |
| Potassium Sorbate | 0.10000 | 0.10000 |
| TOTAL | 100.00000 | 100.00000 |

Both the regular and light margarine spreads contained approximately 3.5 milligrams of policosanol per 8 gram serving size.

EXAMPLE 3

The policosanol preparation, 1.0% policosanol in soybean oil, was used to prepare ranch, French, creamy Italian and thousand island dressings containing plant stanol esters. Table 3 showed the composition of a ranch dressing produced. The process for preparing the ranch dressing in the pilot plant involved the following processing steps. The preservatives (potassium sorbate and sodium benzoate) and EDTA were dissolved in the dressing emulsion tank on a pilot plant size Charlotte Colloid Mill unit. KELTROL T xanthan gum and KELCOLOID LVF (both from Kelco) were dispersed in a portion of the soybean oil (one part gums and 2-5 parts oil). The gum dispersion was hydrated in the water for 10 minutes using medium speed agitation. This was followed by blending in the vinegar and lemon juice, sugar, salt, ranch seasonings, buttermilk solids and titanium dioxide. After mixing the blend at high speed for 10 minutes, the polysorbates were melted and added with the liquid egg yolk and mixed for about one minute. The policosanol oil blend was mixed into the salad oil. The stanol esters (if present) and CAPROL ET (A. C. Humko) were added to the soybean salad oil and the mixture was heated to approximately 130° F. to melt and dissolve CAPROL and stanol esters. While mixing the aqueous phase blend at high speed, the oil blend containing stanol esters (if present), CAPROL ET, policosanol oil blend, vitamin E and tocopherol preparation were added slowly to form the dressing emulsion. The coarse emulsion produced was then milled through a colloid mill with 0.02" gap opening. After the viscosity, titratable acidity, salt and pH were determined and approved, the milled dressing was pumped through a filling unit and bottled.

TABLE 3

Compositions of Typical Cholesterol-Lowering Ranch Dressings Containing Policosanol with or without Stanol Esters

| Ingredient Composition | With Stanol Esters Weight (Pounds) | Without Stanol Ester Weight (Pounds) |
|---|---|---|
| Water | 33.0807 | 36.6479 |
| Vinegar, 120 Grain, White distilled | 7.0000 | 7.0000 |
| Sugar, Fine Granulated | 4.9000 | 4.9000 |
| Ranch Seasoning #139 (Ventura) | 4.2000 | 4.2000 |
| Cultured Buttermilk Solids #64414 (Armour) | 1.6000 | 1.6000 |
| Salt | 0.7000 | 0.7000 |
| Calcium Disodium EDTA | 0.0060 | 0.0060 |
| Egg Yolk, Liquid, 10% Salt | 0.3600 | 0.3600 |
| KELTROL T Xanthan Gum (Kelco) | 0.3500 | 0.3500 |
| Polysorbate 60, Tween 60 | 0.3000 | 0.3000 |
| Lemon Juice Concentrate, 400 GPL | 0.2500 | 0.2500 |
| KELCOLOID LVF, (Kelco) | 0.1750 | 0.1750 |
| Polysorbate 80, TWEEN 80 | 0.1600 | 0.1600 |
| Titanium Dioxide | 0.1400 | 0.1400 |
| Potassium Sorbate | 0.0800 | 0.0800 |
| Sodium Benzoate | 0.0800 | 0.0800 |
| Vitamin E Acetate (Roche) | 0.0183 | 0.0183 |
| Policosanol/soybean oil blend (1:99 w/w) (CHOLESSTANOL policosanol from Garuda International) | 1.2000 | 1.2000 |
| DL-Alpha-Tocopherol (Roche) | 0.0082 | 0.0082 |
| Calcium Disodium EDTA | 0.0060 | 0.0060 |
| Paprika Oleoresin 1000 ASTA | 0.0019 | 0.0019 |
| Soybean Oil, Salad Oil | 38.8186 | 41.1967 |
| Stanol Esters (Raisio) | 5.9453 | 0.0000 |
| CAPROL ET (A. C. Humko) | 0.6200 | 0.6200 |
| TOTAL | 100.0000 | 100.0000 |

Both dressings contained approximately, 3.5 milligram of policosanol per 30 gram serving size.

We claim:

1. A process for preparing a comestible product containing long chain alcohols comprising:
providing a long chain alcohol;
providing an edible oil containing less than about 12 weight percent linolenic acid that is substantially free of medium chain triglycerides composed of $C_8$ to $C_{10}$ fatty acids;
admixing said high molecular alcohols in said edible oil to form a high molecular weight alcohol/edible oil admixture that contains less than two weight percent high molecular weight alcohol, free of an emulsifier, and has a viscosity of less than 200 centipose measured at 70° F.;
and combining said admixture with other components of a comestible product.

2. The process of claim 1 wherein the long chain alcohol is policosanol.

3. The process of claim 1 wherein the long chain alcohol is octacosanol.

4. The process of claim 1 wherein the edible oil is a vegetable oil.

5. The process of claim 1 wherein the comestible product is a non-continuous oil phase product.

6. The process of claim 5 wherein the non-continuous oil phase product is a margarine.

7. The process of claim 5 wherein the non-continuous oil phase product is a spread.

8. The process of claim 5 wherein the non-continuous oil phase product is a salad dressing.

9. The process of claim 4 wherein the non-continuous oil phase product is a mayonnaise.

10. The process of claim 1 wherein the amount of the long chain alcohol admixed in the edible oil comprises from about 0.0001% to about 0.4 weight % of the comestible product.

11. The process of claim 1 wherein the amount of the high molecular weight alcohol admixed in the edible oil comprises from about 0.001% to about 0.01% of the comestible product.

12. Method for preparing a long chain alcohol in an edible oil material comprising:
providing an edible oil substantially free of medium chain triglycerides composed of $C_8$-$C_{10}$ triglycerides and containing less than about 10 weight percent linolenic acid;
providing a long chain alcohol;
admixing said edible oil and long chain alcohol in the presence of an energy source such that the long chain alcohol is admixed in the oil; said long chain alcohol/edible oil admixture is stable and free of an emulsifier or surfactant; and having a viscosity of less than about 200 centipose as measured at 70° F.

13. The method of claim 10 wherein the long chain alcohol and oil are heated to a temperature of from about 160 to about 180° F.

14. The method of claim 11 wherein the long chain alcohol is provided at a level of from about 0.1 to about 2 weight percent based upon the level of the oil.

15. The method of claim 12 wherein the long chain alcohol is policosanol.

16. The method of claim 13 wherein the policosanol has an octacosanol content of greater than about 65 weight percent.

17. A composition comprising:
a stable edible oil/long chain alcohol admixture substantially free of an emulsifying or surfactant agent, the edible oil substantially free of medium chain triglycerides composed of $C_8$-$C_{10}$ triglycerides and containing less than about 10 weight percent linolenic acid;
the admixture having a viscosity of less than about 200 centipoise as measured at 70° F.

18. The composition of claim 15 wherein the long chain alcohol is from about 0.1 to about 2 weight percent of the total composition weight.

19. The composition of claim 16 wherein the long chain alcohol is policosanol.

* * * * *